United States Patent [19]

Shuttleworth et al.

[11] 4,366,321
[45] Dec. 28, 1982

[54] PREPARATION OF 2-HALO-3-NITRO-5-ACYL THIOPHENES AND INTERMEDIATE COMPOUNDS

[75] Inventors: Leslie Shuttleworth, Ormskirk; David Mullen, Liverpool, both of England

[73] Assignee: Eastman Kodak Company, Rochester, N.Y.

[21] Appl. No.: 257,450

[22] Filed: Apr. 24, 1981

Foreign Application Priority Data

[30] Jan. 30, 1981 [GB] United Kingdom ...... 8102948
[51] Int. Cl.³ .................. C07D 333/00; C07D 333/24
[52] U.S. Cl. ........................................ 549/68; 549/75
[58] Field of Search ................................... 549/68, 75

[56] References Cited

U.S. PATENT DOCUMENTS

| | | | |
|---|---|---|---|
| 2,649,461 | 8/1953 | Hermann .............................. | 549/68 |
| 3,822,314 | 7/1974 | Gay et al. .......................... | 549/75 X |
| 4,158,015 | 6/1979 | Paul .................................. | 549/75 X |
| 4,188,203 | 2/1980 | Farge et al. ....................... | 549/75 X |

*Primary Examiner*—Paul F. Shaver
*Attorney, Agent, or Firm*—Donald W. Spurrell; Daniel B. Reece, III

[57] ABSTRACT

Disclosed are novel intermediates and their preparation, and the preparation therefrom of 2-halo-3-nitro-5-acyl thiophenes which themselves are important intermediates for the preparation of azo dyes of the type,

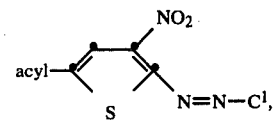

wherein $C^1$ represents typically any aniline, tetrahydroquinoline, benzomorpholine or the like coupler and the acyl group contains from 1–10 carbons. It has been found that if 2-acyl thiophene is treated with a hydroxylamine compound, e.g., a salt of hydroxylamine, including sulphate, chloride or the like, to form the oxime prior to the 2-position halogenation and 3-position nitration steps, various side reactions such as halogenation of the acyl group and nitration of the 5-position are avoided, the yield of each step is improved, and the reactions are less sensitive to the deleterious effects of temperature variations and excess reactants. The oxime derivative is readily reconverted to the acyl derivative after the halogenation and nitration steps have been completed. This product is then readily aminated to give the 2-amino derivative.

9 Claims, No Drawings

PREPARATION OF 2-HALO-3-NITRO-5-ACYL THIOPHENES AND INTERMEDIATE COMPOUNDS

This invention concerns the preparation of 2-halo-3-nitro-5-acyl thiophenes which are important intermediates for the preparation of azo dyes of the type,

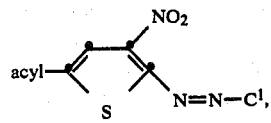

wherein $C^1$ represents typically any aniline, tetrahydroquinoline, benzomorpholine or similar coupler and the acyl group contains from 1–10 carbons. Also concerned are novel intermediates and their preparation. Sucy dyes are disclosed, for example, in U.S. Pat. No. 2,805,218.

An established procedure found in the prior art for the preparation of these thiophenes where the acyl group is acetyl is as follows:

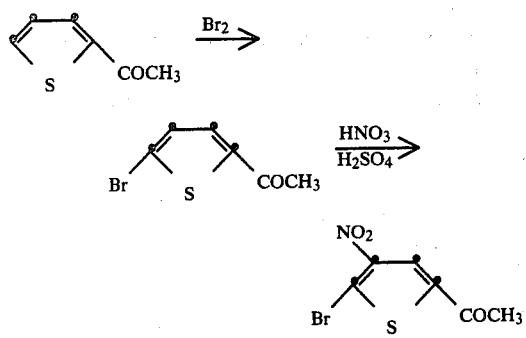

This procedure has the disadvantage, however, in that during the nitration step, some displacement of the acetyl group with nitro occurs, leading to contamination of the product (III) with 2-bromo-3,5-dinitro thiophene. In addition to reducing yield, this side product gives undesirable side reactions during the subsequent amination of (III) to the diazo precursor. Moreover, this displacement depletes the nitric acid which leaves some 2-bromo-5-acetyl thiophene reactant (II) in the reaction medium. Any use of excess nitric acid to avoid this problem, of course, makes the over-nitration still worse. A further disadvantage is that during the bromination step some side chain bromination occurs, leading to the formation of bromoacetyl derivatives which are strongly lachrymatory and very undesirable in commercial production.

In the present invention, it has been found that if 2-acyl thiophene is treated with a hydroxylamine compound e.g. a salt of hydroxylamine, including sulphate and chloride, to form the oxime prior to the bromination and nitration steps, the side reactions described are avoided, the yield of each step is improved, and the reactions are less sensitive to the deleterious effects of temperature variations and excess reactants. The oxime derivative is readily reconverted to the acyl derivative as shown below after the bromination and nitration steps have been completed. This product is then aminated as described below to give the 2-amino derivative.

The invention may be more particularly defined as the process for preparing 2-halo-3-nitro-5-acyl thiophene comprising halogenating 2-acyl thiophene oxime to give 2-halo-5-acyl thiophene oxime, nitrating the same to give 2-halo-3-nitro-5-acyl thiophene oxime, and then reacting the same with a more reactive aldehyde or ketone, such as formaldehyde, having a carbonyl group capable of oxime exchange to give 2-halo-3-nitro-5-acyl thiophene. The novel intermediates formed in the present process and forming part of the present invention have the formulae:

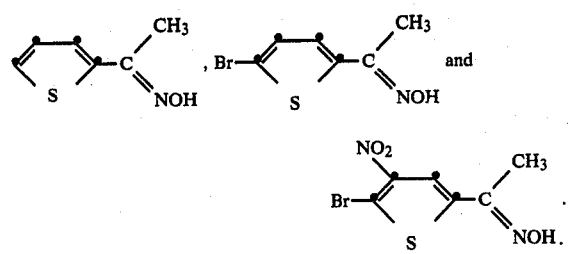

A wide variety of acyl groups may be employed in the present process such as derived from aryl, cycloaliphatic, and straight or branched chain alkyl of 1–10 carbons, and such alkyl substituted with groups which do not impair the ring bromination and nitration.

The present invention and its utility is further illustrated by the following reaction sequence A to E:

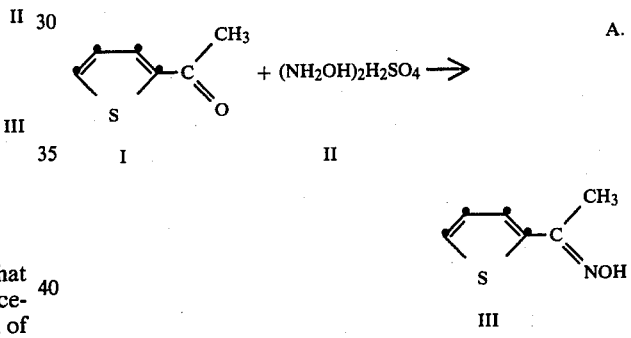

In this reaction, which may be considered a preliminary step in carrying out the overall process, the mole ratio of hydroxylamine to I can be varied widely, e.g. from 1/2 to 5/1 or higher; it being advisable only that enough of II be used to convert all of I to III, i.e. at least a 1/1 mole ratio of hydroxylamine/I. Any base, such as NaOH, may be used to adjust the pH to optimum for condensation with the carbonyl group. The condensation is conveniently carried out at reflux, but lower temperatures can be used with attendant slower reaction rates.

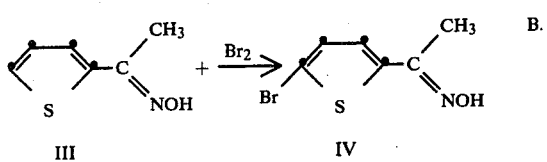

This bromination step is carried out in customary manner without isolating III, using preferably a substantial molar excess of bromine to allow for eliminated HBr. Any convenient solvent, such as acetic acid, may be used as long as side chain bromination catalysts are not present. The bromination temperature can vary between, e.g. 0° C. and 100° C., with from about 15° C. to about 50° C. being preferred.

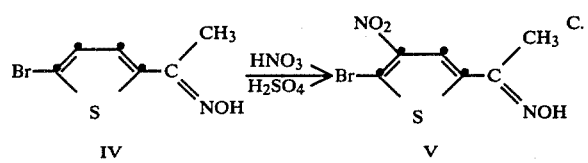

This nitration step is carried out also in customary manner using concentrated or fuming nitric acid in concentrated sulphuric acid, added at a sufficiently low temperature for safety, the overall formation of the nitronium ion being strongly exothermic.

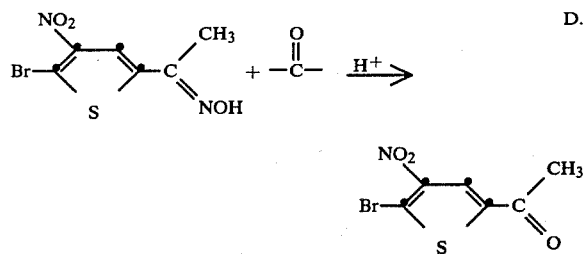

This acid catalyzed displacement reaction may be carried out with a variety of aldehydes or ketones such as formaldehyde, acetone, levulinic acid, and preferably paraformaldehyde, as is well known in the art. A molar excess of carbonyl compound over the oxime is desirable and the temperature of reaction is preferably maintained between 0° C. and 70° C. with 15° C. to 40° C. being most preferred.

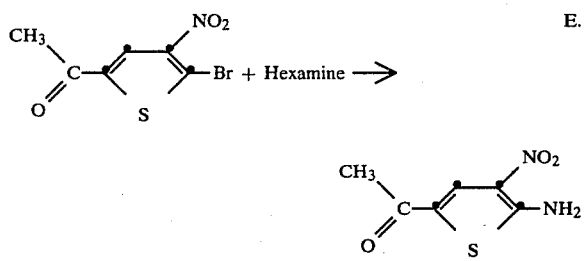

This amination with hexamethylenetetramine (hexamine) in any of a wide variety of solvents gives excellent yield and purity of the amine. In the process, the halogen is replaced with an —NH₂ group and various decomposition products of the hexamethylenetetramine are produced. The reaction temperature is conveniently at reflux but temperatures of, for example, from 0° C. to 200° C. may also be employed, with the maximum temperature limited only by reactant decomposition temperature and other practical considerations. The useful solvent types include protic as well as aprotic, and include alcohols, ethers, petroleum fractions, dimethyl formamide and dimethyl sulphoxide, with water or alcohol being preferred. The ratio of hexamine to halo reactant may vary widely but a molar ratio of from about ⅓ to about 10/1 may be used, for example, with a ratio of 1/1 to 3/1 being preferred. A wide range of solvent proportions may be used, with from about 1 to about 50 ml of solvent per gram of total reactants being preferred. In place of hexamine as a source of —NH₂, any of a wide variety of aminating agents may be employed including gaseous ammonia per se and ammonia released by reaction of ammonium compounds such as NH₄Cl with, for example, Na₂CO₃.

In the halogenation of 2-acetyl thiophene oxime as opposed to halogenation of unprotected 2-acetyl thiophene, it has been shown that ring halogenation is much encouraged by the presence of the oxime group. In an experiment, a mixture of 2-acetyl thiophene and 2-acetyl thiophene oxime was brominated using insufficient bromine for complete bromination such that the two reactants had to compete for available bromine. Analysis of the reaction mixture indicated that the oxime had brominated completely in the ring, and no 2-acetyl thiophene oxime starting material could be detected. Conversely, the analysis indicated that no unprotected 2-acetyl thiophene had in fact brominated, this reagent being left unchanged. Further, the bromination of 2-acetyl thiophene oxime appears to avoid side chain bromination as shown by the lack of lachrymatory characteristics of the product. Additionally, the yield of the bromination reaction is increased when the oxime derivative is used.

The nitration of 2-bromo-5-acetyl thiophene oxime shown above proceeds without any detectable displacement of the oxime functions. This contrasts markedly to the case where the unprotected acetyl derivative is used directly wherein as estimated 15-20% acetyl displacement occurs. Consequently, only stoichiometric quantities of nitric acid need be used in the present process and contamination of the product with either starting material or over nitrated products is essentially eliminated.

The following example will further illustrate the present invention and its utility.

Preparation of 2-Bromo-5-Acetyl Thiophene Oxime

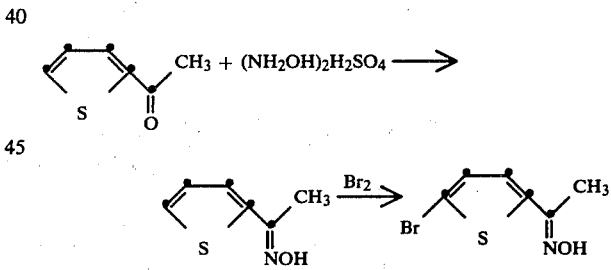

2-Acetylthiophene (25.2 g) (0.2 mole) and hydroxylamine sulphate (16.8 g) (0.102 mole) were stirred together at room temperature in acetic acid (80 g). A solution of sodium hydroxide (20 g NaOH + 40 ml H₂O) was added dropwise, allowing the temperature to rise gradually from the heat of reaction. After addition was complete the mixture was refluxed for 3 hours and then cooled to 30° C.

A solution of bromine (35.2 g) (0.22 mole) in acetic acid (10 g) was added dropwise at 30°-40° C. After the addition, the mixture was stirred further at 50° C. for 15 minutes to complete the reaction, and then cooled back to about 30° C. The mixture was then drowned into cold water, filtered and the solid product washed with water and dried. The yield of the brominated product was 35.6 g (80.9%).

Preparation of 2-Bromo-3-Nitro-5-Acetyl Thiophene

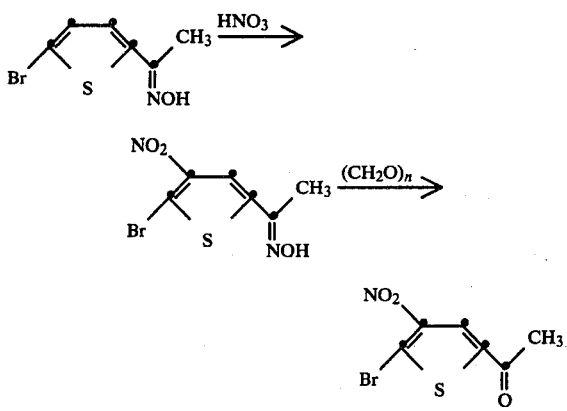

2-Bromo-5-acetyl thiophene oxime (35.2 g) (0.16 mole) was dissolved in concentrated sulphuric acid (80 ml) at 5°–10° C. A mixture of fuming nitric acid (95–98%) (10.6 g) (0.16 mole) in concentrated sulphuric acid (10 ml) was added dropwise at less than 10° C. The temperature, after the addition, was allowed to rise to room temperature and the system stirred there for 60 minutes. Paraformaldehyde (2.0 g) was then added carefully and the mixture stirred at room temperature for 15 minutes. This was followed by the addition of a further amount (15.0 g) of paraformaldehyde at about 20°–26° C. Stirring was continued at this temperature for 2–3 hours further, and then the mixture was drowned into water, stirred for 30 minutes and filtered. The solid 2-bromo-3-nitro-5-acetyl thiophene was washed with water and dried. The yield was 35.3 g (88.25%).

Amination to the Diazotizable Amine

2-Bromo-3-nitro-5-acetyl thiophene (1.0 g) was added to a solution of hexamethylenetetramine (1.0 g) in water (50 ml). The reaction mixture was refluxed for 1 hour, cooled and filtered. The product 2-amino-3-nitro-5-acetyl thiophene was washed with a little water and dried in air. The yield was 0.65 g (83%) mp. 220°–222° C.

We claim:
1. The process for preparing 2-halo-3-nitro-5-acyl thiophene comprising halogenating 2-acyl thiophene oxime to give 2-halo-5-acyl thiophene oxime, nitrating the product to give 2-halo-3-nitro-5-acyl thiophene oxime, and then reacting the oxime with a compound having a carbonyl group capable of oxime exchange to give 2-halo-3-nitro-5-acyl thiophene.
2. The process of claim 1 wherein the acyl group is acetyl.
3. The process of claim 1 wherein the halo substituent is bromine.
4. The process of claim 1 wherein the carbonyl group is obtained from paraformaldehyde.
5. The process of claim 1 wherein the bromination temperature is between 15° C. and 50° C.
6. The process of claim 2 wherein the halo substituent is bromine, and the carbonyl group is obtained from paraformaldehyde.
7. The compound having the formula:

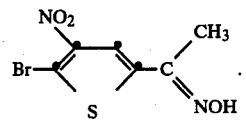

8. The compound having the formula:

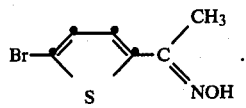

9. The compound having the formula:

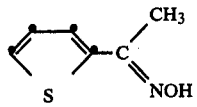

* * * * *